United States Patent [19]

Raes et al.

[11] 4,105,686

[45] Aug. 8, 1978

[54] PROCESS FOR DEACTIVATING TOLUENE DIISOCYANATE DISTILLATION RESIDUE

[75] Inventors: Maurice C. Raes, Branford; Pierrepont Adams, Darien, both of Conn.

[73] Assignee: Olin Corporation, New Haven, Conn.

[21] Appl. No.: 806,806

[22] Filed: Jun. 15, 1977

[51] Int. Cl.² ..................................... C07C 119/048
[52] U.S. Cl. .................... 260/453 PH; 260/453 SP
[58] Field of Search ................. 260/453 PH, 453 SP

[56] References Cited

U.S. PATENT DOCUMENTS 3,914,269  10/1975  Nersasian .................. 260/453 PH

*Primary Examiner*—Dolph H. Torrence
*Attorney, Agent, or Firm*—F. A. Iskander; Thomas P. O'Day; Robert J. Feltovic

[57] ABSTRACT

A selective process wherein toluene diisocyanate distillation residue is converted from a viscous liquid into an inert, granular solid by treatment with an organic acid.

11 Claims, No Drawings

PROCESS FOR DEACTIVATING TOLUENE DIISOCYANATE DISTILLATION RESIDUE

This invention relates to the treatment and processing of the distillation residue which is obtained in the production of toluene diisocyanate. More particularly, the invention relates to a process for converting this residue into an inert, non-toxic and easy-to-handle granular solid.

Toluene diisocyanate is produced on a large commercial scale by a process which comprises reacting toluene diamine with excess phosgene usually in the presence of an organic solvent medium. An illustrative process is disclosed in U.S. Pat. No. 3,287,387. Along with toluene diisocyanate, the phosgenation product mixture usually comprises unreacted phosgene, solvent, hydrogen chloride by-product, and a relatively substantial proportion of side reaction products in the form of residual and high-boiling materials.

Recovery of a substantial or major proportion of toluene diisocyanate from this mixture is achieved by distillation which is usually effected in two or more steps to enable removal of the low-boiling components, e.g., the phosgene and solvent, first before recovering the toluene diisocyanate. The remaining residue from distillation is a viscous, fuming mixture which is difficult to transport or process. Thus on being pumped out for underground burial or incineration, it gets thicker and thicker presumably as a result of further polymerization. As such, it eventually plugs up the lines making if difficult, if not impossible, to continue the pumping operation. Additionally, because of the toxic fumes emanating therefrom, this residue poses an environmental problem. Thus in processing it to underground burial, or incineration, or chemical treatment, special and costly steps must be taken to avoid polluting the atmosphere.

In co-pending U.S. application Ser. No. 780,562, filed on Mar. 23, 1977 by J. R. Cassata, it is taught that the toluene diisocyanate distillation residue can be converted to a non-toxic granular solid by treatment with certain aqueous bases at mildly elevated temperatures, i.e., 60°–150° F. Further in the prior art dealing with toluene diisocyanate distillation residues, U.S. Pat. Nos. 3,128,310 and 3,331,876 disclose the concept of hydrolyzing such residues, at elevated temperatures, i.e., 150° C or higher, and in the presence of caustic, thereby converting such residues to toluene diamine.

U.S. Pat. No. 3,799,963 discloses a process for reducing the acidity and hydrolyzable chloride content of toluene diisocyanate by heating it in the presence of formic acid. Furthermore, according to U.S. Pat. No. 3,350,438, biuret polyisocyanates can be prepared by reacting an organic polyisocyanate with formic acid; and Canadian Pat. No. 751,927 discloses the use of carboxylic acids having at least two carbon atoms to remove metallic or basic impurities from organic diiocyanates.

Now a new process has been found for deactivating the distillation residue which is obtained in the production of toluene diisocyanate. In accordance with the invention, this process comprises heating the residue in the presence of an organic acid. The result of this treatment is to transform the residue from a viscous, fuming material into a non-toxic, inert, granular solid which can then be easily disposed of or processed in open air without creating a toxic hazard or polluting the atmosphere.

More in detail, the process of the inventin can be carried out batch-wise or in a continuous basis. Generally continuous operation is preferred as it is more readily adapted to commercial practice in connection with the continuous production of toluene diisocyanate.

The process applies to the treatment of any residue which results from the distillation of the product of phosgenating toluene diamine. As commonly used in the commercial production of toluene diisocyanate, the toluene diamine is typically made up of a mixture of 2,4- and 2,6-isomers and may in addition contain traces of ortho-toluene diamine. The distillation residue is usually a dark, viscous liquid which is substantially free of solvent. Along with varying amounts of phosgene, by-product hydrochloric acid, and a residual content, up to about 60% by weight of toluene diisocyanate, it usually contains a substantial amount, e.g., 25–70% by weight, of high boiling and tarry by-products of the phosgenation reaction.

The organic acid which is used in practicing the process of the invention can be any such material which is effective in rendering the residue non-toxic. Commonly available such acids which can be used include the monocarboxylic acids generally represented by the formula RCOOH, wherein R is hydrogen or an alkyl group. Usually, the latter contains from 1 to 8 and preferably 1–3 carbon atoms. Thus illustrative acids encompassed by this formula include formic, acetic, propionic, butyric, and higher carbon content monocarboxylic acids.

In addition, di- and tri-functional carboxylic acids may be employed in practicing the process of the invention. Among these, oxalic acid and citric acid are especially preferred due to their ready availability and relatively low cost. By the same token, especially preferred monocarboxylic acids as represented by the above-indicated formula are those in which R is hydrogen, methyl or ethyl, inasmuch as such acids are of relatively low cost. Thus as a group the acids which can be used to economic advantage are formic acid, acetic acid, propionic acid, oxalic acid, and citric acid. Formic and acetic acid are most preferred.

The acid may be used as such, i.e., in pure or full-concentration, or it may be diluted with a suitable, solvent, the latter being an organic solvent or water.

The proportion of the acid which is used per unit weight of the residue varies widely depending on such factors as the particular make-up of the residue, the temperature of the residue-acid mixture, the speed of reaction required, and so on. Thus any suitable proportion may be used which is effective, when mixed with the residue at a temperature as specified hereinbelow, in transforming the residue from a toxic liquid to an inert or non-toxic solid. Illustratively, the proportion of acid may range generally from about 0.05 to about 50 parts per every 100 parts by weight of the residue. Usually, however, a relatively small amount is adequate to achieve the objectives of the invention. Accordingly, for reasons of economy, it is preferable to employ from about 0.1 to about 10, and more preferably about 0.15–5, parts of the acid per every 100 parts by weight of the residue.

In practicing the process of the invention the deactivation of the residue is carried out at elevated temperatures. While any such temperature may be used which is effective in achieving this objective, usually such temperature ranges from about 120° to about 200° C. The reason is that using temperatures outside this range may result in premature, partial solidification of the residue before it has completely deactivated. For instance, large chunks may be obtained which would still have a liquid, toxic core. The use of a temperature within the above-indicated range is of further advantage in two respects. First, it is conducive to a relatively fast reaction between the residue and the acid. Secondly, at a temperature of about 120°–200° C, the residue, though viscous, is still substantially liquid and thus easier to mix and react with the acid.

To achieve a temperature within the above-indicated range, it may be necessary to heat the residue-acid mixture. However, heating may not be necessary where the residue is already hot enough as may be the case when it is immediately obtained from the distillation still and treated in accordance with the invention.

In accordance with the preferred embodiments, the process described herein is carried out at a temperature well within the above-specified range, such as about 130°–175° C and more preferably about 140°–165° C.

The process of the invention may be practiced using any suitable type of reaction zone or vessel which is equipped with an agitator, for adequately mixing the residue with the acid, and with heat transfer means for maintaining the mixture within the above-indicated range. Preferably, the reaction vessel should also be equipped with conventional means for capturing and removing toxic gases, e.g., phosgene, hydrogen chloride and possibly carbon monoxide, which are liberated during the residue deactivation reaction. Such gases may then be processed through appropriate equipment, such as a water scrubber, to avoid atmospheric pollution.

Any convenient order of bringing together the residue and the aqueous acid may be employed. For example, either material may be added to the other, or both materials may be simultaneously charged to the reactor. Transformation of the residue from a dark, viscous liquid to a granular solid takes place fairly rapidly, i.e., usually within a few minutes, after it is mixed with the acid.

The solid material which results is usually granular, or friable, and non-toxic. As such it can be processed in open-air without any danger of polluting the atmosphere or creating a toxic hazard.

The following examples are provided to illustrate the invention. The toluene diisocyanate distillation residue which is referred to and used throughout the examples was obtained by a conventional method, as described for example in U.S. Pat. No. 3,287,387 to Denton et al, for the commercial production of toluene diisocyanate. More specifically, this method involves (a) reacting, at about 125° C, excess phosgene with a solution of toluene diamine (mixture of 2,4- and 2,6-isomers) in monochlorobenzene solvent, (b) removing the monochlorobenzene, and most of the unreacted phosgene and by-product HCl from the phosgenation product, and (c) further distilling the remaining product to recover overhead pure toluene diisocyanate. The residue from this distillation, which contains about 30% by weight of residual toluene diisocyanate, is used in the examples.

Further in the examples, all parts and percentages are by weight unless otherwise specified.

EXAMPLE I

A three-neck flask was used which was equipped with a mechanical agitator, a heating mantle, a thermometer, a watercooled reflux condenser, a nitrogen gas inlet tube and a Dean Stark trap. Two hundred grams of residue were placed in the flask. Then 2.4 grams (1.2%) of formic acid were added and mixed in while maintaining the temperature of the mixture at about 150° C. Liberated gases, made up of phosgene, hydrogen chloride, and carbon dioxide, were removed by means of a slow nitrogen stream to a water scrubber. As a result of this treatment, the residue solidifed practically instantaneously. After cooling to room temperature, the solids were found to be of a friable or granular consistency and non-toxic as evidenced by the absence of any gases of fumes emanating therefrom.

EXAMPLE II

Substantially the same result was obtained in this example which was an exact repetition of Example I except that acetic acid was used in lieu of formic acid.

EXAMPLE III

The procedure of Example I was repeated after adjusting the toluene diisocyanate content of the residue to 40% by the addition of pure toluene diisocyanate. Because of this increase in the toluene diisocyanate content, the 1.2% of formic acid was found insufficient to bring about solidification of the residue. Accordingly, an additional amount was added making the total formic acid used 2.5%. After cooling to room temperature, the residue completely solidified to a granular consistency.

What is claimed is:

1. A process for converting into an inert solid the residue which is obtained from the distillation of the product of phosgenating toluene diamine to the corresponding toluene diisocyanate, which process comprises mixing said residue, at a temperature from about 120° C to about 180° C, with an effective amount of organic acid selected from the group consisting of oxalic acid, citric acid, and a monocarboxylic acid represented by the formula:

RCOOH wherein R is hydrogen or an alkyl group having from 1 to 8 carbon atoms.

2. The process of claim 1 wherein said acid is formic acid or acetic acid.

3. The process of claim 1 wherein said temperature ranges from about 140° to about 160° C.

4. The process of claim 1 wherein said acid is employed in a proportion of about 0.15 to about 5 parts per every 100 parts by weight of said residue.

5. The process of claim 1 wherein said alkyl group contains 1 to 3 carbon atoms.

6. The process of claim 5 wherein said temperature is about 130°–170° C.

7. The process of claim 6 wherein said acid is employed in a proportion from about 0.1 to about 10 parts per every 100 parts by weight of said residue.

8. The process of claim 6 wherein said acid is selected from the group consisting of formic acid, acetic acid, propionic acid, oxalic acid, and citric acid.

9. The process of claim 8 wherein said proportion is about 0.15 to about 5 parts per every 100 parts by weight of said residue.

10. The process of claim 9 wherein said acid is formic acid or acetic acid.

11. The process of claim 10 wherein said temperature is about 140°–160° C.

* * * * *